US012758672B2

(12) United States Patent
Bruder et al.

(10) Patent No.: US 12,758,672 B2
(45) Date of Patent: Oct. 13, 2026

(54) SCENT DISPENSING SYSTEM

(71) Applicant: Chimera Technology LLC, Palatine, IL (US)

(72) Inventors: Geoffrey A Bruder, Rocky River, OH (US); David Flood, Palatine, IL (US)

(73) Assignee: CHIMERA TECHNOLOGY LLC, Palatine, IL (US)

(*) Notice: Subject to any disclaimer, the term of this patent is extended or adjusted under 35 U.S.C. 154(b) by 697 days.

(21) Appl. No.: 17/897,454

(22) Filed: Aug. 29, 2022

(65) Prior Publication Data

US 2023/0094659 A1 Mar. 30, 2023

Related U.S. Application Data

(60) Provisional application No. 63/248,959, filed on Sep. 27, 2021.

(51) Int. Cl.
*A61L 9/12* (2006.01)
*A61L 9/14* (2006.01)

(52) U.S. Cl.
CPC ................ *A61L 9/125* (2013.01); *A61L 9/14* (2013.01); *A61L 2209/111* (2013.01); *A61L 2209/134* (2013.01); *A61L 2209/135* (2013.01)

(58) Field of Classification Search
CPC .................................. A61L 9/14; A61L 9/125
See application file for complete search history.

(56) References Cited

U.S. PATENT DOCUMENTS

| | | | | |
|---|---|---|---|---|
| 2006/0175426 | A1 | 8/2006 | Schramm | |
| 2008/0073443 | A1* | 3/2008 | Tollens | B05B 17/0646 222/638 |
| 2017/0274405 | A1* | 9/2017 | Lucas | B05B 17/0661 |
| 2018/0326112 | A1* | 11/2018 | Mushtaq | H04L 51/046 |
| 2019/0083719 | A1* | 3/2019 | Freeman | A61L 9/14 |
| 2020/0009285 | A1* | 1/2020 | Take | A61L 9/125 |
| 2020/0078485 | A1 | 3/2020 | Suarez et al. | |
| 2020/0139388 | A1 | 5/2020 | Stout et al. | |
| 2021/0213153 | A1* | 7/2021 | Kwok | A61M 15/08 |

FOREIGN PATENT DOCUMENTS

| | | | |
|---|---|---|---|
| WO | 2016164917 | A1 | 10/2016 |
| WO | 2018/022562 | A1 | 2/2018 |
| WO | 2019151948 | A1 | 8/2019 |
| WO | 2020/035244 | A1 | 2/2020 |

OTHER PUBLICATIONS

UKIPO—Combined Search and Examination Report under Sections 17 and 18(3) for serial No. GB2214087.5; issued on Mar. 27, 2023.

Extended European Search Report for EP22197677.2, issued on Feb. 14, 2023.

(Continued)

*Primary Examiner* — Donald R Spamer
*Assistant Examiner* — Kayla Rose Sarantakos
(74) *Attorney, Agent, or Firm* — Flener IP & Business Law

(57) ABSTRACT

A scent dispensing system comprises a plurality of storage tanks containing a liquid medium of terpenes, scent agents, and/or flavoring agents, and one or more dispensing devices that are adapted to deliver atomized liquid medium from the plurality of storage tanks to produce a scent selection for a user.

12 Claims, 6 Drawing Sheets

(56) References Cited

OTHER PUBLICATIONS

CIPO—Office Action for serial No. 3,175,837; dated Jan. 25, 2024; Canada.
CIPO—Voluntary Amendment for serial No. 3,175,837; filed Jan. 31, 2025; Canada; Alex Ross.
CIPO—Response and Amendments to Office Action dated Jan. 25, 2024 for serial No. 3,175,837; filed Feb. 5, 2025; Canada; Alex Ross.
CIPO—Notice of Allowance for serial No. 3,175,837; dated Sep. 9, 2025; Canada.
Applicant response to Extended European Search Report dated Feb. 14, 2023 for European Patent Application No. 22197677.2 filed on Jul. 26, 2023.
Communication pursuant to Article 94(3) EPC for European Patent Application No. 22197677.2, Mailed Mar. 13, 2024.
Applicant response to Communication pursuant to Article 94(3) dated Mar. 14, 2024 for European Patent Application No. 22197677.2 filed on Jun. 14, 2024.
Communication pursuant to Article 94(3) EPC for European Patent Application No. 22197677.2, Mailed Feb. 19, 2025.
Applicant response to Communication pursuant to Article 94(3) dated Feb. 19, 2025 for European Patent Application No. 22197677.2 filed on May 27, 2025.
Communication under Rule 71(3) EPC for EP 22197677.2, Mailed Oct. 28, 2025.
Decision to Grant for European patent 4154919 Pursuant to Article 97(1) EPC; mailed Mar. 12, 2026.

* cited by examiner

SCENT DISPENSING SYSTEM

CROSS-REFERENCE TO RELATED APPLICATIONS

This application claims the priority benefit of U.S. Provisional Application No. 63/248,959, filed on Sep. 27, 2021 and incorporated herein by reference in its entirety.

FIELD OF THE DISCLOSURE

The present disclosure relates to a scent dispensing system, and more particularly to a scent dispensing system for Cannabinoid containing products.

BACKGROUND

The 2018 Farm Bill legalized the sale of cannabinoid containing products in the United States provided that Delta-9 THC content was kept below 0.3% in the plant and product. Cannabinoid containing products are becoming ubiquitous in the market and the variety of products available are difficult for consumers to understand. Educating the consumer about the process of production, from seed to sale, as well as informing them about the chemical compounds within the product is a challenge due to the tactile nature of the end product. It would be advantageous to allow customers to smell cannabinoid containing products before deciding to purchase them. A need therefore exists for a scent dispensing system having a user interface that allows a user to choose a Cannabinoid containing product and be provided with the scent of the chosen product.

BRIEF SUMMARY OF THE INVENTION

In an aspect of the invention, a scent dispensing system comprises a plurality of storage tanks containing a liquid medium of terpenes, scent agents, and/or flavoring agents, and one or more dispensing devices that are adapted to deliver atomized liquid medium from the plurality of storage tanks to produce a scent selection for a user.

In another aspect of the invention, a scent dispensing system comprises a plurality of storage tanks containing a liquid medium of terpenes, scent agents, and/or flavoring agents, and one or more dispensing devices that are adapted to deliver atomized liquid medium from the plurality of storage tanks to produce a scent selection for a user. Each of the one or more dispensing devices further comprises a vapor generator connected to a supply of water, wherein each vapor generator is adapted to deliver a cloud of water vapor for the user.

In a further aspect of the invention, a scent dispensing system comprises a plurality of storage tanks containing a liquid medium of terpenes, scent agents, and/or flavoring agents, and one or more dispensing devices that are adapted to deliver atomized liquid medium from the plurality of storage tanks to produce a scent selection for a user. One or more pumps are disposed between the plurality of storage tanks and the one or more dispensing devices, wherein thee one or more pumps are adapted to pump the liquid medium from the storage tanks to the one or more dispensing devices.

DETAILED DESCRIPTION

Figure 1:
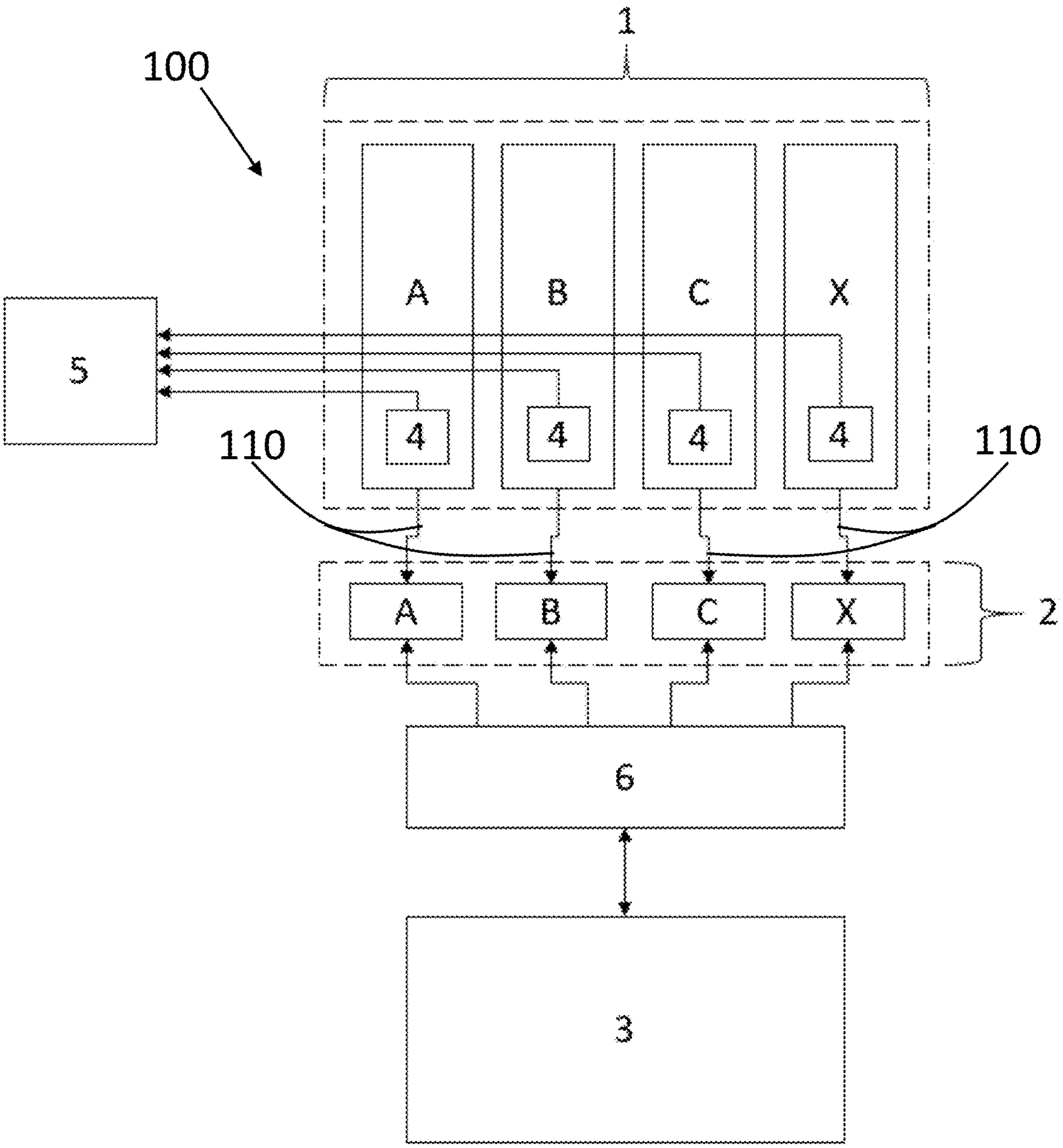
FIG. 1 shows a scent dispensing system, according to an embodiment.
Figure 2:
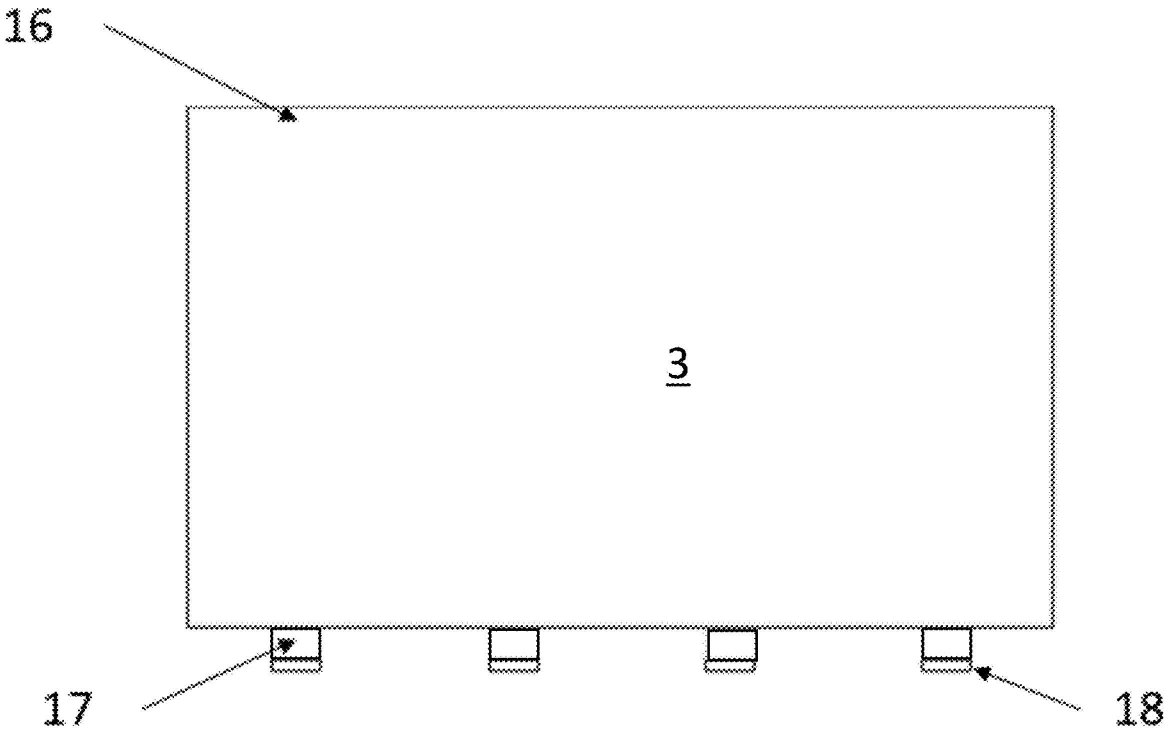
FIG. 2 shows a schematic representation of a user interface, according to an embodiment.

Referring to FIG. 1, an embodiment of a scent dispensing system 100 comprises a plurality of storage tanks 1 (that are individually labeled as A, B, C, X). In an embodiment each of the plurality of storage tanks 1 holds a liquid medium, for example without limitation, comprising terpenes, and/or other scent and flavoring agents that mimic the smell of a desired component to be delivered by the system 100. In an embodiment the liquid medium may also comprise a thinning agent, for example without limitation water, an oil, or an alcohol, wherein the thinning agent enables the concentration of the final delivered liquid to be adjusted. In an embodiment the plurality of storage tanks 1 is made of a corrosion resistant material, for example without limitation stainless steel, aluminum, glass, or polyvinylchloride (PVC), wherein each of the storage tanks 1 is sealed against leaking.

In an embodiment each of the plurality of storage tanks 1 is connected to a dispensing device 2 (having individual receiving modules labeled as A, B, C, X) either directly or through corrosion resistant connections 110, wherein the connections 110 can be made, for example without limitation, from stainless steel, aluminum, protective lined Tygon®, or PVC tubing. In an embodiment all of the plurality of storage tanks 1 connect to a single dispensing device 2; however, in other embodiments the plurality of storage tanks 1 connects to a plurality of dispensing devices 2.

Still referring to FIG. 1, in an embodiment a system controller 6 is in electrical communication with and receives input data from a user interface 3. In an embodiment the system controller 6 is in electrical communication with and transmits control signals generated from the input data to the one or more dispensing devices 2. Electrical communication for data transfer between any of the components described herein can be via a wired connection or via a wireless connection using any wireless protocol as is known in the art.

In an embodiment the system controller 6 stores data regarding interactions with the user interface 3, for example input data regarding the selection of product scents to sample. In an embodiment the system controller 6 is connected to the internet allowing remote monitoring and/or troubleshooting of the system controller 6, and further allowing software used by the system controller 6 to reside on a cloud-based platform and be deployed to multiple system controllers 6 within multiple scent dispensing systems 100.

Still referring to FIG. 1, in an embodiment the user interface 3 is an analog interface, for example, comprising buttons and/or switches. In an embodiment the user interface 3 is a digital interface, for example, comprising a touchscreen. In an embodiment the user interface 3 is a combination analog and digital interface.

In an embodiment the user interface 3 conveys information to a user about one or more chemical compounds to be delivered via the one or more dispensing devices 2. In an embodiment the user interface 3 allows a user to select which compound they would like to smell and select or toggle a selection input which in turn sends a signal to the system controller 6.

Figure 3:
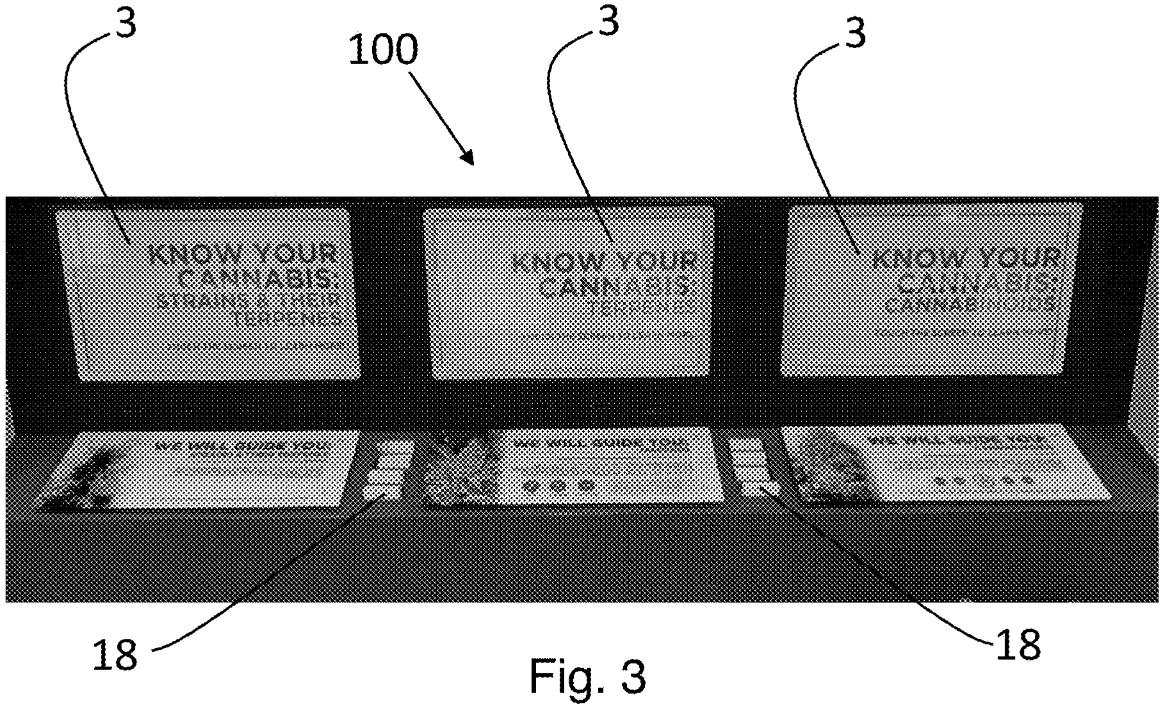
FIG. 3 shows a photograph of an exemplary scent dispensing system, according to an embodiment.

Referring to FIG. 3, in an embodiment a user interface 3 comprises a touchscreen 16, a plurality of dispensers blocks 17 and a plurality of dispensing ports 18. Each dispensing port 18 is the physical location where a user will smell and see vaporized fluid delivered from the plurality of storage tanks 1. FIG. 3 shows a photograph of an installation of an exemplary scent dispensing system 100 having three user interfaces 3 and eight dispensing ports 18.

Figure 4:
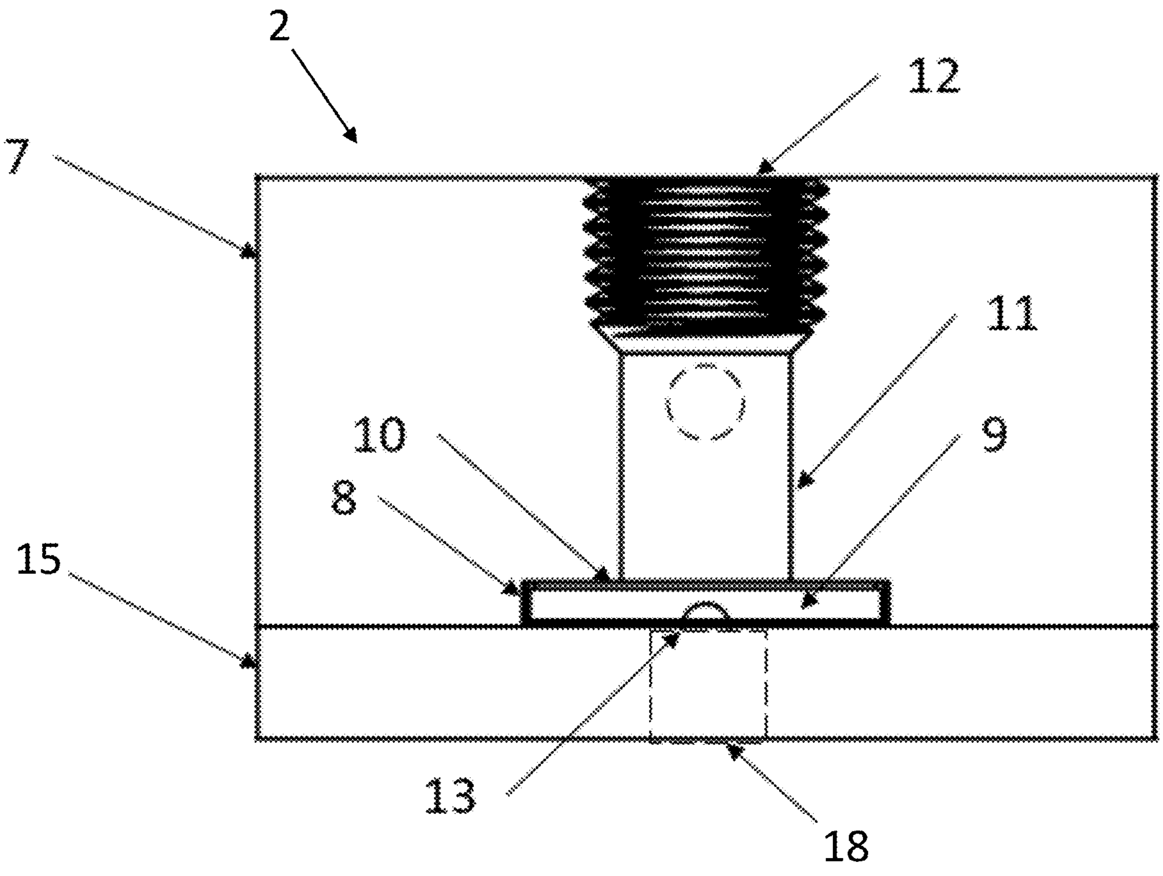
FIG. 4 shows an exemplary dispensing device, according to an embodiment.

In an embodiment the one or more dispensing devices 2 deliver a scent from the storage tanks 1 to a user. Along with the scent, in an embodiment a visible atomization cloud is generated. Referring to FIG. 4, in an embodiment a main block 7 comprises an interface between the storage tanks 1 and an atomization device 9. In an embodiment the main block 7 is made of a corrosion resistant material such as stainless steel, aluminum, or PVC. In an embodiment the main block 7 comprises a storage tank connection 12, transport passage 11, atomizer cavity 8, and one or more mounting point (not shown). In an embodiment the storage tank connection 12 is a threaded connection, hose barb, push connection, or the like, which fluidly connects the main block 7 to a storage tank 1 while remaining leak-proof. In another embodiment the storage tank connection 12 and the transport passage 11 are part of a tube or hose or pipe (see 110 in FIG. 1) that connects the storage tanks 1 to the one or more dispensing devices 2.

Still referring to FIG. 4, in an embodiment the transport passage 11 allows liquid to flow from the storage tank connection 12 to the atomizer cavity 8 at which point the liquid contacts the atomization device 9. In an embodiment the atomizer cavity 8 provides a volume which securely contains the atomization device 9 and an atomizer seal 10. In an embodiment the atomizer seal 10 is a malleable material that, for example, provides a liquid tight seal around the atomization device 9 when compressed between the main block 7 and a clamp block 15.

In an embodiment the clamp clock 15 is secured to the main block 7, for example, by being bolted, clamped or otherwise affixed in a manner that maintains compression of the atomizer seal 10 throughout operation, but is removable to allow for servicing. In an embodiment the clamp block 15 further comprises a dispensing port 18 which allows for vaporized liquid to exit the atomization device 9 and reach the user. In an embodiment an electrical connection port 13 is contained wholly within the main block 7, within the clamp block 15, or partially within both. In an embodiment the electrical connection port 13 allows for wiring from the system controller 6 to reach the atomization device 9. In an embodiment the atomization device 9 is piezoelectric; however, in other embodiments the atomization device 9 is pneumatic, or another sort of liquid atomization device that is electrically actuated.

Figure 5:
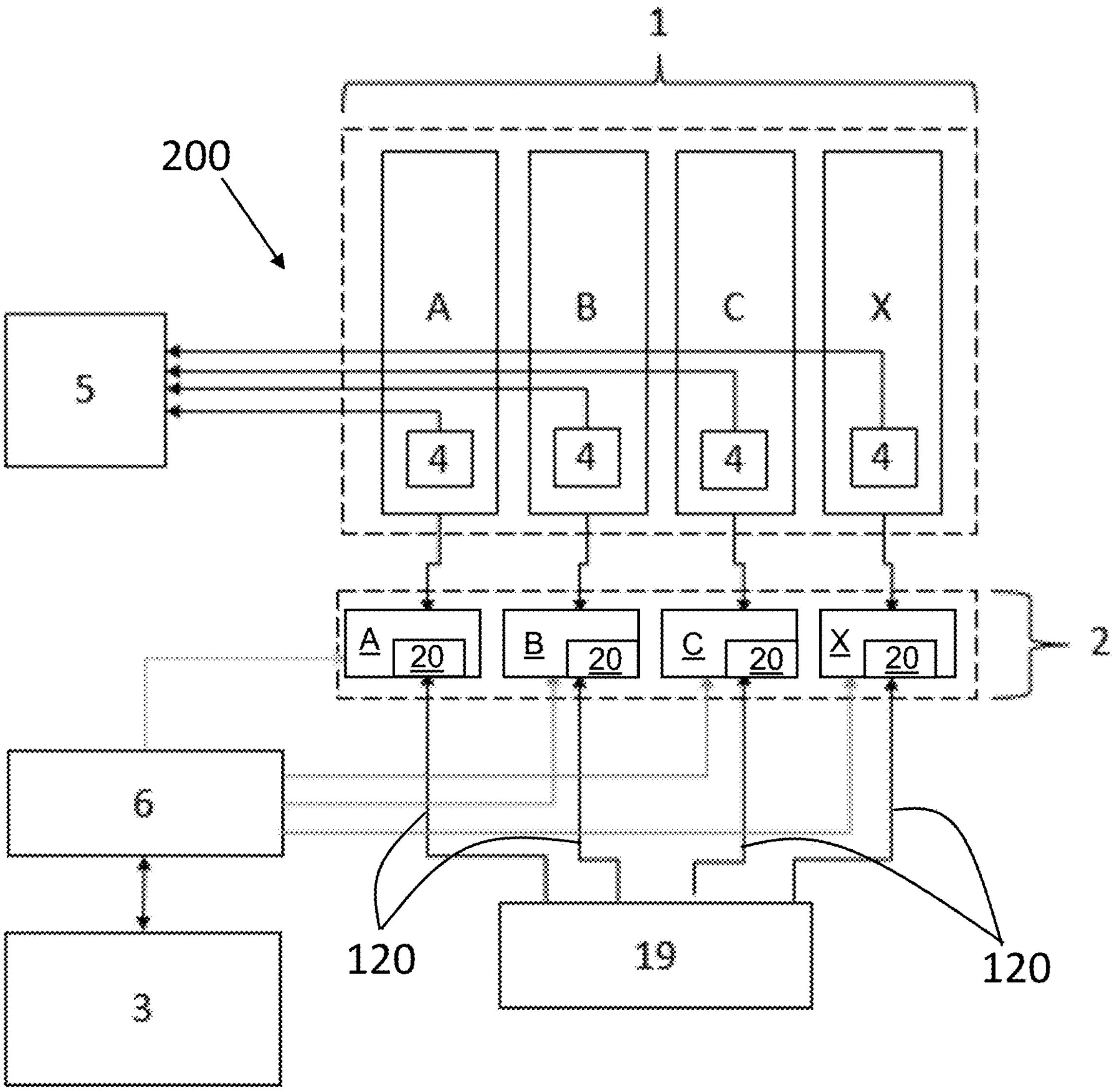
FIG. 5 shows a scent dispensing system, according to another embodiment.
Figure 6:
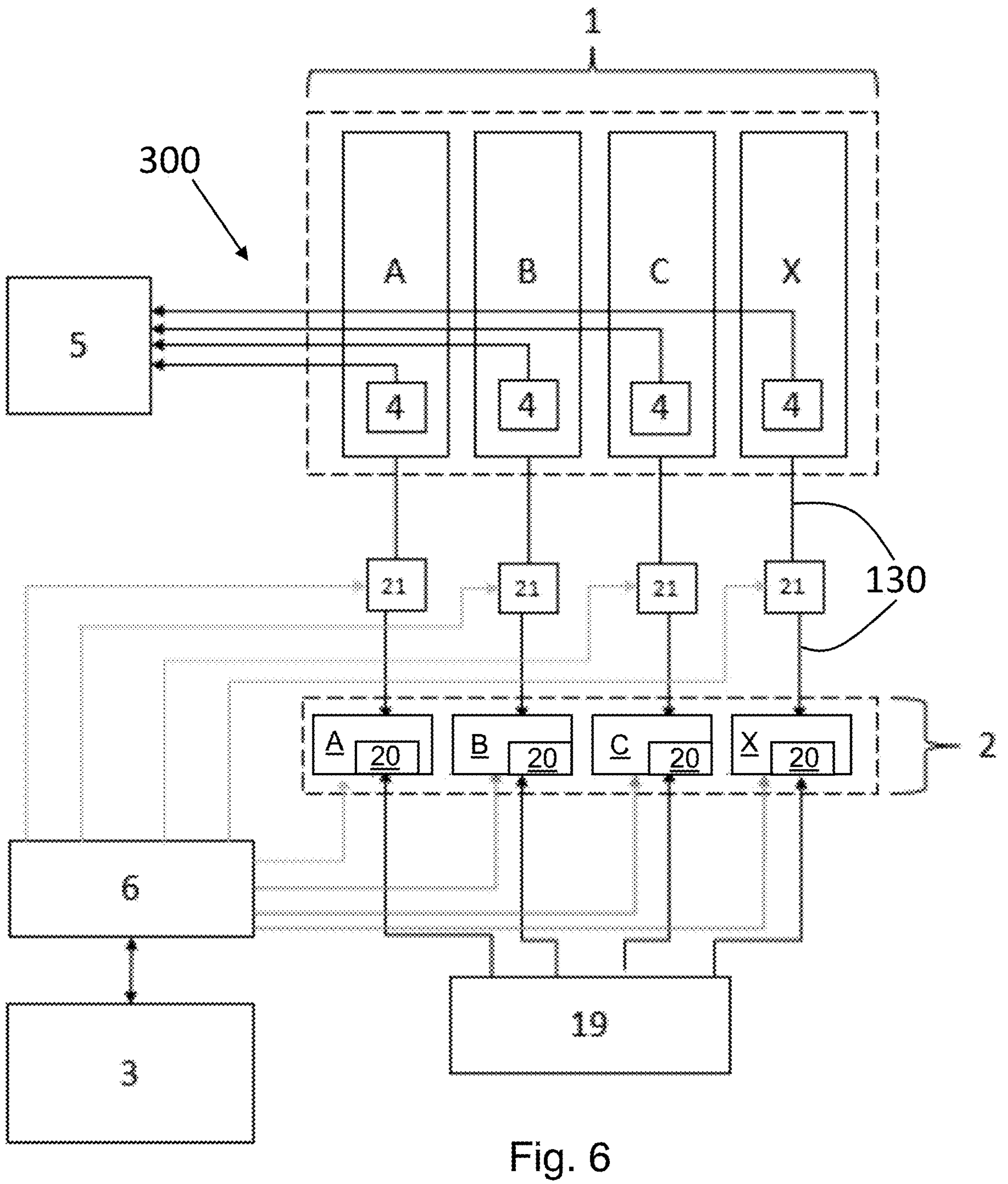
FIG. 6 shows a scent dispensing system, according to a further embodiment.

Referring to FIGS. 1, 5, and 6, in an embodiment, within each storage tank 1 is disposed a level sensor 4, which is electronically connected to a level control unit 5. In an embodiment the level sensor 4 within a storage tank 1 transmits an electrical signal to the level control unit 5 when the liquid within the storage tank 1 reaches a low setpoint, whereupon the level control unit 5 then communicates an alarm to an operator. In an embodiment the level control unit 5 is integrated into the system controller 6; however, in another embodiment the level control unit 5 is a stand-alone unit. Furthermore, in an embodiment the level control unit 5 records data to determine which liquid is most frequently utilized.

Referring to FIG. 5, an embodiment of a scent dispensing system 200 includes a water tank 19 and a vapor generator 20. In an embodiment the water tank 19 is a container made of glass, PVC, or another metal or plastic that resists corrosion with prolonged exposure to water. In an embodiment the water tank 19 is connected to the vapor generator 20 by flexible or rigid tubing 120 that is metal or plastic that resists biological buildup and corrosion with prolonged exposure to water. In an embodiment the water tank 19 is disposed above the vapor generator 20 such that gravity allows water to flow into the vapor generator 20 when actuated. In an embodiment the water lines 120 from the water tank 19 may connect in series to all the vapor generators 20 rather than by individual connections so long as the vapor generators 20 are successively lower in elevation, thereby allowing gravity to feed them in succession. In an embodiment a valve (not shown) may be placed at the lowest and highest points within the water lines 120 to allow air to be bled from the water lines 120. In an embodiment as a user selects a compound to smell, the system controller 6 sends a signal to the vapor generator 20, which releases a visible mist of water vapor utilizing water from the water tank 19 along with the desired scent, by actuating the appropriate dispensing device 2.

Referring to FIG. 6, an embodiment of a scent dispensing system 300 includes a plurality of pumps 21, for example without limitation, chemical resistant pumps 21 such as a diesel fuel transfer pump, in the scent dispensing path. In an embodiment the plurality of pumps 21 is connected to between the plurality of storage tanks 1 and the one or more dispensing devices 2 through corrosion resistant connections 130, wherein the connections 130 can be made, for example without limitation, from stainless steel, aluminum, protective lined Tygon®, or PVC tubing. In an embodiment the plurality of pumps 21 is controlled, electrically, via the system controller 6.

Upon a user selecting a scent via the user interface 3, in an embodiment the system controller 6 sends an electrical signal to the plurality of pumps 21, which pumps the scent containing liquid medium from the plurality of storage tanks 1 to the one or more dispensing devices 2. In an embodiment that utilizes the plurality of pumps 21, the plurality of storage tanks 1 can be disposed below the one or more dispensing devices 2 to move the liquid medium against gravity.

As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INDUSTRIAL APPLICABILITY

A scent dispensing system comprises a plurality of storage tanks containing a liquid medium of terpenes, scent agents, and/or flavoring agents, and one or more dispensing devices that are adapted to deliver atomized liquid medium from the plurality of storage tanks to produce a scent selection for a user. In an embodiment each of the one or more dispensing devices further comprises a vapor generator connected to a supply of water, wherein each vapor generator is adapted to deliver a cloud of water vapor for the user. In another embodiment one or more pumps are disposed between the plurality of storage tanks and the one or more dispensing devices, wherein the one or more pumps are adapted to pump the liquid medium from the storage tanks to the one or more dispensing devices. The scent dispensing system can be manufactured in industry for use by consumers.

Numerous modifications to the present invention will be apparent to those skilled in the art in view of the foregoing description. It is not desired to limit the invention to the exact construction and operation shown and described, and accordingly, all suitable modifications and equivalents may be resorted to, falling within the scope of the invention. Accordingly, this description is to be construed as illustrative only of the principles of the invention and is presented for the purpose of enabling those skilled in the art to make and use the invention and to teach the best mode of carrying out same. The exclusive rights to all modifications which come within the scope of the appended claims are reserved. All patents, patent publications and applications, and other references cited herein are incorporated by reference herein in their entirety.

We claim:

1. A scent dispensing system, comprising:

a plurality of storage tanks, each said storage tank containing a different liquid medium selected from the group consisting of terpenes, scent agents, flavoring agents and combinations thereof;

a corresponding plurality of dispensing devices, each said dispensing device coupled to a respective storage tank and comprising an atomization device configured to generate atomized liquid medium from the respective storage tank; and a corresponding plurality of dispensing ports, each said dispensing port adapted to deliver the atomized liquid medium from the respective dispensing device to an external environment to produce a scent selection for a user;

wherein each of the plurality of dispensing devices further comprises:

a corresponding vapor generator connected to a supply of water, wherein each corresponding vapor generator is adapted to deliver a separate visible cloud of water vapor, along with the scent selection upon actuation of one of the dispensing devices.

2. The scent dispensing system of claim 1, further comprising a user interface adapted to receive the scent selection from a user, and a system controller electrically connected to the user interface and to the plurality of dispensing devices, wherein the system controller receives input data regarding the scent selection and transmits control signals to the plurality of dispensing devices.

3. The scent dispensing system of claim 2, wherein the system controller stores data regarding interactions with the user interface and wherein the data regarding interactions comprises data regarding user selection of discrete scents to sample.

4. The scent dispensing system of claim 3, wherein the system controller is Internet connected and uses software that resides on a cloud-based platform which is deployed by multiple system controllers within multiple scent dispensing systems, and wherein the data regarding user selection of discrete scents to sample is remotely monitored by the multiple system controllers via the Internet connection.

5. A scent dispensing system, comprising:

a plurality of storage tanks, each said storage tank containing a different liquid medium selected from the group consisting of terpenes, scent agents, flavoring agents and combinations thereof;

a corresponding plurality of dispensing devices, each said dispensing device coupled to a respective storage tank and comprising an atomization device configured to generate atomized liquid medium from the respective storage tank;

a corresponding plurality of dispensing ports, each said dispensing port adapted to deliver the atomized liquid medium from the respective dispensing device to an external environment to produce a scent selection for a user; and one or more pumps disposed between the plurality of storage tanks and the corresponding plurality of dispensing devices, wherein the one or more pumps are adapted to pump the liquid medium from the storage tanks to the corresponding dispensing devices, and wherein each of the plurality of dispensing devices further comprises:

a vapor generator connected to a supply of water, each vapor generator is adapted to deliver a separate visible cloud of water vapor, along with the scent selection upon actuation of one of the dispensing devices.

6. The scent dispensing system of claim 5, wherein the one or more pumps are chemical resistant pumps.

7. The scent dispensing system of claim 5, wherein each vapor generator is adapted to deliver the separate visible cloud of water vapor concurrently with the delivery of the atomized liquid medium.

8. A scent dispensing system, comprising:

a plurality of storage tanks containing a liquid medium selected from the group consisting of terpenes, scent agents, flavoring agents and combinations thereof;

one or more dispensing devices that are adapted to deliver atomized liquid medium from the plurality of storage tanks to produce a scent selection for a user; wherein each of the one or more dispensing devices further comprises a vapor generator connected to a supply of water, wherein each vapor generator is adapted to deliver a separate visible cloud of water vapor for the user, along with the scent selection upon actuation of one of the dispensing devices.

9. The scent dispensing system of claim 8, wherein the one or more dispensing devices and the vapor generators therein are adapted to respectively deliver the atomized liquid medium and the water vapor concurrently.

10. The scent dispensing system of claim 8, further comprising a user interface adapted to receive the scent selection from a user, and a system controller electrically connected to the user interface and to the one or more dispensing devices, wherein the system controller receives input data regarding the scent selection and transmits control signals to the one or more dispensing devices.

11. The scent dispensing system of claim 10, wherein the system controller stores data regarding interactions with the user interface.

12. The scent dispensing system of claim 10, wherein the system controller is internet connected.

* * * * *